US010124246B2

(12) United States Patent
Yanev et al.

(10) Patent No.: US 10,124,246 B2
(45) Date of Patent: Nov. 13, 2018

(54) PRESSURE SENSITIVE PERIPHERAL DEVICES, AND ASSOCIATED METHODS OF USE

(71) Applicant: ActivBody, Inc., Aliso Viejo, CA (US)

(72) Inventors: Kostadin Dimitrov Yanev, Alamo, CA (US); Ivo Kostadinov Yanev, Sofia (BG); Ludmil Borissov Kalaydjiyski, Royal Wootton Bassett (GB)

(73) Assignee: ACTIVBODY, INC., Aliso Viejo, CA (US)

( * ) Notice: Subject to any disclaimer, the term of this patent is extended or adjusted under 35 U.S.C. 154(b) by 328 days.

(21) Appl. No.: 14/257,868

(22) Filed: Apr. 21, 2014

(65) Prior Publication Data

US 2015/0301613 A1    Oct. 22, 2015

(51) Int. Cl.
*A63F 13/06* (2006.01)
*A63F 13/20* (2014.01)
(Continued)

(52) U.S. Cl.
CPC ............ *A63F 13/06* (2013.01); *A61B 5/6897* (2013.01); *G06F 3/0338* (2013.01);
(Continued)

(58) Field of Classification Search
CPC ....................................................... A63F 13/06
See application file for complete search history.

(56) References Cited

U.S. PATENT DOCUMENTS

| 4,577,625 A | 3/1986 | Lohati et al. ................... 128/57 |
| 4,702,108 A | 10/1987 | Amundsen | |

(Continued)

FOREIGN PATENT DOCUMENTS

| CN | 201270095 | 8/2009 |
| EP | 2284646 A1 | 2/2011 |

(Continued)

OTHER PUBLICATIONS

"Fitness Made Fun", WiiFit™, Instruction Booklet, copyright 2008 Nintendo, 28 pages.

(Continued)

*Primary Examiner* — Dmitry Suhol
*Assistant Examiner* — Ankit Doshi
(74) *Attorney, Agent, or Firm* — Pillsbury Winthrop Shaw Pittman LLP (57) ABSTRACT

Facilitating a user to provide inputs to a computing platform by applying varying pressure to one or more external points on a pressure sensitive peripheral device is disclosed. The pressure sensitive peripheral device may include one or more pressure sensors disposed within a housing body or housing bodies of the pressure sensitive peripheral device. The pressure sensors may provide pressure signals conveying information associated with compressive forces applied to the housing body or bodies of the pressure sensitive peripheral device. Inputs to control one or more aspects of a computing platform coupled to the pressure sensitive peripheral device may be provided based on the pressure signals. The one or more aspects of the computing platform may include one or more aspects of a graphical user interface on a display associated with the computing platform, operational aspects of the computing platform and/or any other aspects of the computing platform.

27 Claims, 4 Drawing Sheets

(51) Int. Cl.
  *G06F 3/0338*      (2013.01)
  *G06F 3/038*       (2013.01)
  *G06F 3/041*       (2006.01)
  *A61B 5/00*        (2006.01)
  *G06F 19/00*       (2018.01)
  *A61B 5/021*       (2006.01)
  *A63B 71/06*       (2006.01)
  *A61B 5/024*       (2006.01)
  *A63B 21/02*       (2006.01)
  *A63B 23/035*      (2006.01)
  *A63B 23/16*       (2006.01)
  *A63B 21/00*       (2006.01)

(52) U.S. Cl.
  CPC .......... *G06F 3/0383* (2013.01); *G06F 3/0414* (2013.01); *G06F 19/00* (2013.01); *G06F 19/3481* (2013.01); *A61B 5/021* (2013.01); *A61B 5/02438* (2013.01); *A63B 21/028* (2013.01); *A63B 21/4035* (2015.10); *A63B 23/03508* (2013.01); *A63B 23/16* (2013.01); *A63B 71/0622* (2013.01); *A63B 2220/51* (2013.01); *A63B 2220/56* (2013.01); *A63B 2225/50* (2013.01)

(56) References Cited

U.S. PATENT DOCUMENTS

| | | | |
|---|---|---|---|
| 4,824,103 A | 4/1989 | Smidt | 272/125 |
| 4,988,981 A | 1/1991 | Zimmerman | |
| 5,144,284 A | 9/1992 | Hammett | |
| 5,242,348 A | 9/1993 | Bates | 482/105 |
| 5,471,405 A | 11/1995 | Marsh | 364/556 |
| 5,702,323 A | 12/1997 | Poulton | |
| 5,720,711 A | 2/1998 | Bond | |
| 5,790,102 A | 8/1998 | Nassimi | 345/163 |
| 5,792,080 A | 8/1998 | Ookawa et al. | 601/115 |
| 5,890,995 A | 4/1999 | Bobick et al. | 482/4 |
| 5,904,639 A | 5/1999 | Smyser et al. | 482/91 |
| 5,923,318 A | 7/1999 | Zhai | |
| 5,982,342 A | 11/1999 | Iwata | |
| 5,997,489 A | 12/1999 | Iwamoto et al. | 601/73 |
| 6,013,007 A | 1/2000 | Root et al. | 482/8 |
| 6,063,045 A | 5/2000 | Wax | |
| 6,126,572 A | 10/2000 | Smith | 482/4 |
| 6,183,425 B1 | 2/2001 | Whalen et al. | 600/592 |
| 6,191,773 B1 | 2/2001 | Maruno | |
| 6,222,465 B1 | 4/2001 | Kumar | |
| 6,227,968 B1 | 5/2001 | Suzuki et al. | 463/7 |
| 6,324,557 B1 | 11/2001 | Chan | |
| 6,359,611 B2 | 3/2002 | Chan | 345/156 |
| 6,360,597 B1 | 3/2002 | Hubbard, Jr. | 73/172 |
| 6,405,278 B1 | 6/2002 | Liepe | 711/103 |
| 6,435,937 B1 | 8/2002 | Naegele | |
| 6,504,530 B1 | 1/2003 | Wilson et al. | |
| 6,513,532 B2 | 2/2003 | Mault et al. | 128/921 |
| 6,585,668 B2 | 7/2003 | Nissim | |
| 6,595,901 B2 | 7/2003 | Reinbold et al. | 482/91 |
| 6,597,347 B1 | 7/2003 | Yasutake | |
| 6,605,038 B1 | 8/2003 | Teller et al. | 600/300 |
| 6,616,579 B1 | 9/2003 | Reinbold et al. | 482/91 |
| 6,662,651 B1 | 12/2003 | Roth | |
| 6,675,130 B2 | 1/2004 | Kanevsky et al. | 702/188 |
| 6,776,345 B1 | 8/2004 | Liang | 235/462 |
| 6,807,869 B2 | 10/2004 | Farringdon et al. | 73/862.046 |
| 6,837,827 B1 | 1/2005 | Lee et al. | 482/8 |
| 6,914,695 B2 | 7/2005 | Walters et al. | 358/1.15 |
| 6,956,833 B1 | 10/2005 | Yukie et al. | 370/328 |
| 6,975,644 B2 | 12/2005 | Tordera et al. | 370/463 |
| 7,026,940 B2 | 4/2006 | Cherubini | |
| 7,121,982 B2 | 10/2006 | Feldman | |
| 7,161,490 B2 | 1/2007 | Huiban | |
| 7,169,120 B2 | 1/2007 | Murdock et al. | 601/129 |
| 7,192,387 B2 | 3/2007 | Mendel | |
| 7,229,385 B2 | 6/2007 | Freeman et al. | 482/4 |
| 7,292,867 B2 | 11/2007 | Werner et al. | 455/456.3 |
| 7,303,534 B2 | 12/2007 | Kahn | 600/587 |
| 7,398,151 B1 | 7/2008 | Burrell et al. | 701/200 |
| 7,429,251 B2 | 9/2008 | Tanizawa et al. | 601/94 |
| 7,468,968 B2 | 12/2008 | Svensson et al. | 370/338 |
| 7,480,512 B2 | 1/2009 | Graham et al. | 455/456.3 |
| 7,499,746 B2 | 3/2009 | Buhlmann et al. | 607/2 |
| 7,517,327 B1 | 4/2009 | Knight | 601/46 |
| 7,526,314 B2 | 4/2009 | Kennedy | 455/556.1 |
| 7,526,954 B2 | 5/2009 | Haselhurst et al. | 73/172 |
| RE40,891 E | 9/2009 | Yasutake | |
| 7,643,895 B2 | 1/2010 | Gupta et al. | 700/94 |
| 7,666,118 B1 | 2/2010 | Anthony | |
| 7,699,755 B2 | 4/2010 | Feldman | |
| 7,699,757 B2 | 4/2010 | Clem et al. | 482/49 |
| 7,702,821 B2 | 4/2010 | Feinberg et al. | 710/13 |
| 7,717,825 B2 | 5/2010 | Van Der Hoeven | |
| 7,758,469 B2 | 7/2010 | Dyer et al. | 482/4 |
| 7,789,800 B1 | 9/2010 | Watterson et al. | 482/8 |
| 7,840,346 B2 | 11/2010 | Huhtala | |
| 7,909,741 B2 | 3/2011 | Kim | |
| 7,975,543 B2 | 7/2011 | Clem | |
| 8,009,056 B2 | 8/2011 | Greene | |
| 8,025,606 B2 | 9/2011 | Hamilton | |
| 8,027,822 B2 | 9/2011 | Turgiss et al. | 703/11 |
| 8,172,723 B1 | 5/2012 | Yanev et al. | 482/8 |
| 8,200,323 B2 | 6/2012 | DiBenedetto | |
| 8,203,454 B2 | 6/2012 | Knight | |
| 8,287,434 B2 | 10/2012 | Zavadsky | |
| 8,343,013 B1 | 1/2013 | Yanev et al. | 482/8 |
| 8,491,446 B2 | 7/2013 | Hinds | |
| 8,618,400 B2 | 12/2013 | Murphy | |
| 8,935,438 B1 | 1/2015 | Ivanchenko | |
| 2001/0049470 A1 | 12/2001 | Mault et al. | 600/300 |
| 2002/0146670 A1 | 10/2002 | Selles et al. | 434/247 |
| 2003/0020629 A1 | 1/2003 | Swartz | |
| 2003/0040688 A1 | 2/2003 | Bauer | 601/23 |
| 2003/0093012 A1 | 5/2003 | Smyser | |
| 2003/0137495 A1 | 7/2003 | Canova | |
| 2004/0021681 A1 | 2/2004 | Liao | 345/702 |
| 2004/0058305 A1 | 3/2004 | Lurie | |
| 2004/0110602 A1 | 6/2004 | Feldman | |
| 2004/0176226 A1 | 9/2004 | Carlson | |
| 2004/0260215 A1 | 12/2004 | Kim | 601/99 |
| 2005/0040999 A1 | 2/2005 | Numano | |
| 2005/0130742 A1 | 6/2005 | Feldman | |
| 2005/0177054 A1 | 8/2005 | Yi | |
| 2005/0209049 A1 | 9/2005 | Shields | |
| 2005/0219355 A1 | 10/2005 | Tahara | |
| 2005/0283204 A1 | 12/2005 | Buhlmann | |
| 2006/0035762 A1 | 2/2006 | Smyser | |
| 2006/0064042 A1 | 3/2006 | Smyser | |
| 2006/0100899 A1 | 5/2006 | Tajima | 705/2 |
| 2006/0122819 A1 | 6/2006 | Carmel | |
| 2006/0247095 A1 | 11/2006 | Rummerfield | |
| 2007/0155589 A1 | 1/2007 | Shimizu | |
| 2007/0024736 A1 | 2/2007 | Matsuda | |
| 2007/0051842 A1 | 3/2007 | Pryor | 242/378.3 |
| 2007/0113681 A1 | 5/2007 | Nishimura et al. | |
| 2007/0184953 A1 | 8/2007 | Luberski | |
| 2007/0219059 A1 | 9/2007 | Schwartz et al. | 482/8 |
| 2007/0219469 A1 | 9/2007 | Vardy | |
| 2007/0232455 A1 | 10/2007 | Hanoun | |
| 2007/0249975 A1 | 10/2007 | Pan et al. | 601/118 |
| 2007/0270727 A1 | 11/2007 | KhorassaniZadeh | |
| 2008/0090703 A1 | 4/2008 | Rosenberg | 492/8 |
| 2008/0091762 A1 | 4/2008 | Neuhauser et al. | 709/201 |
| 2008/0096726 A1 | 4/2008 | Riley et al. | 482/8 |
| 2008/0100718 A1 | 5/2008 | Louks et al. | 348/211.2 |
| 2008/0101272 A1 | 5/2008 | Hayes et al. | 370/313 |
| 2008/0132388 A1 | 6/2008 | Clem | |
| 2008/0146336 A1* | 6/2008 | Feldman | A63F 13/02 463/37 |
| 2008/0161051 A1 | 7/2008 | Schobbert et al. | 455/558 |
| 2008/0171311 A1 | 7/2008 | Centen | |
| 2008/0261696 A1 | 10/2008 | Yamazaki | |
| 2008/0262918 A1 | 10/2008 | Wiener | 705/14 |
| 2008/0281234 A1 | 11/2008 | Goris | |

(56) References Cited

U.S. PATENT DOCUMENTS

| | | | |
|---|---|---|---|
| 2008/0287832 A1 | 11/2008 | Collins et al. | 600/587 |
| 2008/0300055 A1 | 12/2008 | Lutnick | |
| 2009/0017993 A1 | 1/2009 | Khanicheh | |
| 2009/0020343 A1 | 1/2009 | Rothkopf et al. | |
| 2009/0025475 A1 | 1/2009 | DeBeliso | |
| 2009/0035740 A1 | 2/2009 | Reed | |
| 2009/0048021 A1 | 2/2009 | Lian | |
| 2009/0048070 A1 | 2/2009 | Vincent et al. | 482/8 |
| 2009/0069160 A1 | 3/2009 | Summers | |
| 2009/0076855 A1 | 3/2009 | McCord | 705/3 |
| 2009/0098980 A1 | 4/2009 | Waters | |
| 2009/0144080 A1 | 6/2009 | Gray et al. | 705/2 |
| 2009/0148821 A1 | 6/2009 | Carkner et al. | 434/265 |
| 2009/0228068 A1 | 9/2009 | Buhlmann et al. | 607/48 |
| 2009/0286654 A1 | 11/2009 | Rice | |
| 2010/0021876 A1 | 1/2010 | Clash | |
| 2010/0265179 A1 | 1/2010 | Ram | 345/163 |
| 2010/0056341 A1 | 3/2010 | Ellis | |
| 2010/0069148 A1 | 3/2010 | Cargill | 463/25 |
| 2010/0087763 A1 | 4/2010 | Hane-Karr | 601/137 |
| 2010/0127983 A1 | 5/2010 | Irani | |
| 2010/0137105 A1 | 6/2010 | McLaughlin | |
| 2010/0178981 A1 | 7/2010 | Holcomb | |
| 2010/0197462 A1 | 8/2010 | Piane | |
| 2010/0245239 A1 | 9/2010 | Sternberg | |
| 2010/0248822 A1 | 9/2010 | Migos | |
| 2010/0255862 A1 | 10/2010 | Mitsunaga | |
| 2010/0255957 A1 | 10/2010 | Clem | |
| 2010/0259472 A1 | 10/2010 | Radivojevic | |
| 2010/0273610 A1 | 10/2010 | Johnson | |
| 2010/0292050 A1 | 11/2010 | DiBenedetto et al. | 482/9 |
| 2010/0292600 A1 | 11/2010 | DiBenedetto et al. | 600/520 |
| 2011/0035303 A1 | 2/2011 | Jakstadt et al. | 705/34 |
| 2011/0046687 A1 | 2/2011 | Naschberger | |
| 2011/0086747 A1 | 4/2011 | Broderick | |
| 2011/0124470 A1 | 5/2011 | Spurling | |
| 2011/0125866 A1 | 5/2011 | Williams | |
| 2011/0143769 A1 | 6/2011 | Jones | |
| 2011/0165998 A1 | 7/2011 | Lau | |
| 2011/0187660 A1 | 8/2011 | Hirata | |
| 2011/0251021 A1 | 10/2011 | Zavadsky et al. | 482/5 |
| 2011/0254777 A1 | 10/2011 | Campbell | |
| 2011/0260987 A1 | 10/2011 | Zhao et al. | 345/173 |
| 2011/0291943 A1 | 12/2011 | Thorn et al. | 345/173 |
| 2011/0302694 A1 | 12/2011 | Wang | |
| 2012/0047465 A1 | 2/2012 | Noda | |
| 2012/0051596 A1 | 3/2012 | Darnell | |
| 2012/0058861 A1 | 3/2012 | Satut | |
| 2012/0066591 A1 | 3/2012 | Hackwell | |
| 2012/0071732 A1 | 3/2012 | Grey et al. | 600/301 |
| 2012/0075236 A1 | 3/2012 | Kim | |
| 2012/0077163 A1 | 3/2012 | SucarSuccar | |
| 2012/0078113 A1 | 3/2012 | Whitestone | |
| 2012/0088553 A1 | 4/2012 | Nunes | |
| 2012/0098744 A1 | 4/2012 | Stinson | |
| 2012/0108394 A1 | 5/2012 | Jones | |
| 2012/0112922 A1 | 5/2012 | Hillis | |
| 2012/0113019 A1 | 5/2012 | Anderson | |
| 2012/0116550 A1 | 5/2012 | Hoffman et al. | 700/91 |
| 2012/0126941 A1 | 5/2012 | Coggill | |
| 2012/0150074 A1 | 6/2012 | Yanev et al. | 600/587 |
| 2012/0162080 A1 | 6/2012 | Cao | 345/168 |
| 2012/0260220 A1 | 10/2012 | Griffin | |
| 2012/0265112 A1 | 10/2012 | Chen | 601/115 |
| 2012/0274508 A1 | 11/2012 | Brown | |
| 2012/0306782 A1 | 12/2012 | Seo et al. | 345/173 |
| 2013/0009907 A1 | 1/2013 | Rosenberg | |
| 2013/0059696 A1 | 3/2013 | Hijmans | |
| 2013/0072301 A1 | 3/2013 | Mallinson | |
| 2013/0076649 A1 | 3/2013 | Myers | |
| 2013/0093679 A1 | 4/2013 | Dickinson | |
| 2013/0106155 A1 | 5/2013 | Chang | |
| 2013/0127748 A1 | 5/2013 | Vertegaal | |
| 2013/0127980 A1 | 5/2013 | Haddick | |
| 2013/0201316 A1 | 8/2013 | Binder | |
| 2013/0212674 A1 | 8/2013 | Boger | |
| 2013/0337974 A1 | 12/2013 | Yanev et al. | 482/8 |
| 2013/0337975 A1 | 12/2013 | Yanev et al. | 482/8 |
| 2013/0337976 A1 | 12/2013 | Yanev et al. | 482/8 |
| 2013/0344919 A1 | 12/2013 | Kim | |
| 2013/0345608 A1 | 12/2013 | Ehrenreich | |
| 2014/0062682 A1 | 3/2014 | Birnbaum | |
| 2014/0123003 A1 | 5/2014 | Song | |
| 2014/0184496 A1 | 7/2014 | Gribetz | |
| 2014/0317722 A1 | 10/2014 | Tartz | |
| 2014/0333543 A1 | 11/2014 | Yanev | |
| 2014/0335494 A1 | 11/2014 | Yanev | |
| 2015/0015476 A1 | 1/2015 | Yanev | |
| 2015/0173993 A1 | 6/2015 | Walsh | |

FOREIGN PATENT DOCUMENTS

| | | |
|---|---|---|
| EP | 2532392 A2 | 12/2012 |
| JP | 2006345990 | 12/2006 |
| JP | 2009142333 | 7/2009 |
| JP | 2010524094 | 7/2010 |
| JP | 2013172841 | 9/2013 |
| TW | 509566 | 1/1988 |
| TW | 201000175 A | 1/2010 |
| TW | 201300098 | 1/2013 |
| TW | 201301215 | 1/2013 |
| WO | WO 2007/025382 | 3/2007 |
| WO | WO 2012/078718 | 6/2012 |
| WO | WO 2013/192071 | 12/2013 |
| WO | WO 2013/192079 | 12/2013 |
| WO | WO 2013/192084 | 12/2013 |
| WO | 2014018049 | 1/2014 |
| WO | 2014182729 | 11/2014 |
| WO | 2014182735 | 11/2014 |
| WO | 2015006411 | 1/2015 |
| WO | 2015006413 | 1/2015 |

OTHER PUBLICATIONS

Jovanov et al., "A Wireless Body Area Network of Intelligent Motion Sensors for Computer Assisted Physical Rehabilitation", *Journal of NeuroEngineering and Rehabilitation*, Mar. 1, 2005, vol. 2, No. 6, retrieved from URL: http://www.jneuroengrehab.com/content/2/1/6, retrieved on Apr. 2, 2012, 10 pages.

Halfbakery, "Computer Mouse with Pressure Sensitive Button", printed from http://www.halfbakery.com/idea/Computer_20Mouse_20with_20pressure . . . , Cord, May 10, 2005, printed Apr. 4, 2014, 3 pages.

International Search Report and Written Opinion dated Apr. 20, 2012 for corresponding International Patent Application No. PCT/US2011/063678 (7 pages).

International Search Report and Written Opinion dated Mar. 13, 2015 for corresponding International Patent Application No. PCT/US2014/037012, 9 pages.

International Search Report and Written Opinion dated Mar. 4, 2015 for corresponding International Patent Application No. PCT/US2014/037018, 9 pages.

International Search Report and Written Opinion dated Nov. 22, 2013 for corresponding International Patent Application No. PCT/US2013/046082 (7 pages).

International Search Report and Written Opinion dated Nov. 7, 2014 for corresponding International Patent Application No. PCT/EPUS2014/045899 (7 pages).

International Search Report and Written Opinion dated Oct. 1, 2013 for corresponding International Patent Application No. PCT/US2013/046096 (10 pages).

International Search Report and Written Opinion dated Oct. 2, 2013 for corresponding International Patent Application No. PCT/US2013/046118 (10 pages).

European Patent Office, European Office Action for EP Application No. 15782873.2, dated Jun. 16, 2018, pp. 1-7.

\* cited by examiner

PRESSURE SENSITIVE PERIPHERAL DEVICES, AND ASSOCIATED METHODS OF USE

FIELD OF THE DISCLOSURE

This disclosure relates to facilitating user input to a computing platform with the user input being facilitated through pressure or force applied to a pressure sensitive peripheral device.

BACKGROUND

Peripheral devices (e.g., computer mice, gamepads, joysticks, driving wheels, remote controls, trackball mice, portable pointing devices, and/or other peripheral devices) for providing inputs to computing platforms are generally known. These devices may be typically configured to facilitate translation of two dimensional or three dimensional motions into control inputs. For example, a computer mouse may enable a user to provide inputs for controlling a graphical user interface (e.g., moving a cursor, selecting items, and/or other control inputs) on a display of a computing platform by clicking buttons on the computer mouse and/or moving the computer mouse on a surface. As another example, a joystick may enable the user to provide the control inputs by pivoting the stick on a base of the joystick.

SUMMARY

One aspect of the disclosure relates to a peripheral device configured to facilitate user input to a computing platform through a pressure sensor disposed at the peripheral device. As used herein, such a peripheral device may be referred to as a pressure sensitive peripheral device. Exemplary implementations may allow a user to simply squeeze the pressure sensitive peripheral device to provide inputs to a computing platform coupled to the pressure sensitive peripheral device. A user may achieve this by applying compressive pressure to the pressure sensitive peripheral device by applying opposing forces to a housing body or housing bodies of the pressure sensitive peripheral device. The inputs so provided by the user may be used to control one or more aspects of the computing platform. This may enhance control of the computing platform by enabling the user to provide extra sets of inputs through squeezing the pressure sensitive peripheral devices. In some implementations, the pressure sensitive peripheral device may facilitate physical exercise by the user. Such exercise may include isometric exercise, dynamic exercise, and/or other types of exercise that involve squeezing, compressing, and/or otherwise applying a pressure and/or force to the pressure sensitive peripheral device. The pressure sensitive peripheral device may be configured to quantify information associated with the physical exercise and/or information associated with the health or wellness of the user.

In some implementations, the pressure sensitive peripheral device may include components such as a heart rate sensor, blood pressure sensor, vibration sensor, accelerometer, user interface, electronic circuitry configured to process signals, and/or any other components for providing additional inputs to the computing platform.

A pressure sensitive peripheral device may comprise a housing body. The housing body may be configured to house a pressure sensor of the pressure sensitive peripheral device. The pressure sensor may be configured to provide a pressure signal conveying information associated with a compressive pressure applied to the housing body. In some implementations, the pressure signal may be provided responsive to the housing body being squeezed by two opposing forces applied to opposing surfaces of the housing body. By way of non-limiting example, one of the opposing forces may be provided by a body part of a user (e.g., finger, hand, knee, and/or other body parts), a fixed surface (e.g., a tabletop, a doorway, and/or other fixed surface), an accessory (e.g., a strap, a stick, and/or other accessory), and/or other objects.

The pressure sensor may be configured to transmit the pressure signal to electronic circuitry for processing. In exemplary implementations, the electronic circuitry may include, without limitation, processor circuits disposed within the pressure sensitive peripheral device (e.g., disposed within the housing body of the pressure sensitive peripheral device), circuitry included in the computing platform, and/or any other types of electronic circuitry. The electronic circuitry may be configured to receive the pressure signal provided by the pressure sensor and provide inputs to the computing platform based on the pressure signal received from the pressure sensor. The electronic circuitry may include a signal component configured to receive and process pressure signals provided by the pressure sensors; an input provision component configured to provide an input to the computing platform based on the received pressures signals for controlling one or more aspects of the computing platform. The inputs may be used to control one or more aspects of a graphical user interface on a display associated with the computing platform.

By way of non-limiting example, the one or more aspects of the graphical user interface may include one or more of input of a value, selection from a menu, scrolling, moving a pointer, manipulation of a virtual object, entry of a password or a code by the user in the graphical user interface, interaction with a fitness program, interaction with a rehabilitation program, interaction with a medical treatment program, interaction with a game by the user through the graphical user interface, and/or other aspects of the graphical user interface.

In some implementations, the inputs provided based on the pressure signal may be used to control operational aspects of the computing platform that does not necessarily involve controlling of graphical user interface on a display associated with the computing platform. For example, a user may be enabled to adjust the volume a level of a sound output by the computing platform, turn on or off the computing platform, adjust the resolution of a video output by the computing platform, switch between network mode (e.g., connected through Wi-Fi) or non-network mode (e.g., no network connections), adjust brightness of the display coupled to the computing platform, and/or any other operational aspects of the computing platform.

A value inputted based on the pressure signal may be an analog value or a digital value. Digital values having very fine granularity may be interpreted by a user as quasi-analog input. By way of non-limiting example, a user may squeeze the pressure sensitive peripheral device with varying forces in order to enter a value on a quasi-analog meter presented on the display where smaller forces correspond to smaller values on the meter and larger forces correspond to larger values on the meter. As another example, a user may enter a height of the user in a text field presented on the display where smaller forces correspond to shorter heights and larger forces correspond to taller heights.

Entry of a password or code based on the pressure signal may be achieved by a sequence of squeezes performed on the pressure sensitive peripheral device. For example, a user may perform different magnitudes and/or different durations of squeezes on the pressure sensitive peripheral device. To illustrate, a user may perform a specific combination of short and long squeezes on the pressure sensitive peripheral device as a password. Combinations of squeezes on different locations of the pressure sensitive peripheral device may be used as a password, according to some implementations.

Manipulation of a virtual object based on the pressure signal may be further based on an accelerometer signal conveying a position and/or a change in position of the pressure sensitive peripheral device. For example, a virtual object may be "grasped" by squeezing the pressure sensitive peripheral device. The position of the virtual object may be controlled through corresponding a position and/or a change in position of the pressure sensitive peripheral device. The accelerometer signal may be provided by an accelerometer (not depicted) and/or other position detection device included in the pressure sensitive peripheral device. In one implementation, exertion and release of pressure may respectively result in zoom-in and zoom-out of a three-dimensional virtual space.

A fitness program may include squeezing pressure sensitive peripheral device. This may be used during isometric and/or dynamic exercise routines. The fitness program may include squeezing the pressure sensitive peripheral device with a threshold force, for a threshold duration of time, for a number of repetitions, moving the pressure sensitive peripheral device along a curve line while squeezing the pressure sensitive peripheral device, a fitness program consist of count base exercises (example push-ups) when the device with count the number of repetition and/or other exercise metrics.

A game may include game actions that may be initiated by user through squeezing the pressure sensitive peripheral device. The game actions may include movement with a force (e.g., thrusting, dashing, turbo charge, and/or other movements), a combat action with a force (e.g., jabbing, heaving, waving with a corresponding force, and/or other combat actions), firing a shot, changing camera angles, selecting next weapon, accelerating, looking around, changing virtual character/units/avatar under control, and/or any other game actions.

The pressure sensor may be configured to provide multiple contemporaneous pressure signals to the electronic circuitry for processing. The electronic circuitry may be configured to interpret the multiple contemporaneous pressure signals and provide the control input to the computing platform based on the interpretation.

In some implementations, the pressure signals provided by the pressure sensor for controlling the one or more aspects of operation of the pressure sensitive peripheral device may be interpreted based on a position on the pressure sensitive peripheral device on which the opposing forces were applied. By way of non-limiting example, squeezing front and rear surfaces of the pressure sensitive peripheral device may correspond to one input, while squeezing top and bottom surfaces of the pressure sensitive peripheral device may correspond to another input.

In some implementations, the compressive pressure applied to the housing body may be quantified on an arbitrary scale such as a scale between one and ten, a scale between one and five stars, and/or other arbitrary scale. For example, without limitation, the compressive pressure or force (or other suitable metric) applied to the housing body may be quantified in absolute units such as pounds (lb), kilograms (kg), Newtons (N), pounds per square inch (PSI), Pascals (Pa), Newtons per meters squared (N/m$^2$), and/or other absolute units.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
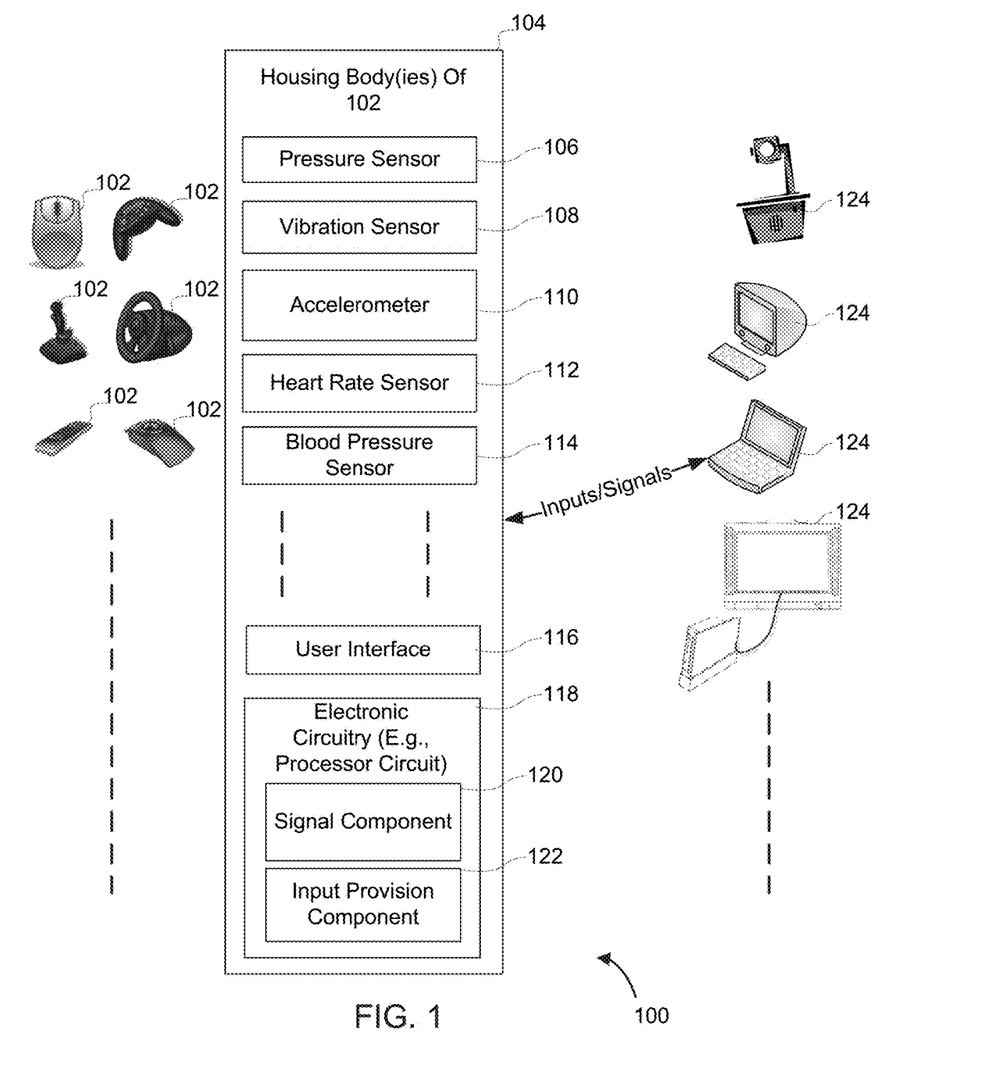
FIG. 1 illustrates a system configured to facilitate receipt of user input using a pressure sensitive peripheral device with a pressure sensor, in accordance with one or more implementations.

FIG. 1 illustrates a system 100 configured to facilitate receipt of user input to a computing platform 124 using a pressure sensitive peripheral device 102 with a pressure sensor 106 disposed within a housing body 104 of the pressure sensitive peripheral device 102, in accordance with one or more implementations. As illustrated, examples of a pressure sensitive peripheral device 102 may include a pressure sensitive device having a form factor similar to a mouse, a gamepad, a joystick, a driving wheel, a remote control, a trackball, and/or any other peripheral devices. As also illustrated, examples of computing platform 124 may include a laptop computer, a desktop computer, a projector system, a game console, a netbook, a smart TV, a settop box, and any other computing platforms 124. It should be understood that the examples of pressure sensitive peripheral device 102 and the computing platforms 124 are not intended to be limiting and include any variations of the examples numerated. For example a pressure-sensitive device can be integrated into the computing platform 124, or can communicate with it via a wireless connection. For instance, pressure sensitive peripheral device 102 having a mouse-like form factor in accordance with the disclosure may include a mechanical, optical, laser, 3-D, tactile, ergonomic, gaming, and/or any other kinds of mouse technologies.

Exemplary implementations of pressure sensitive peripheral device 102 may allow a user to simply squeeze pressure sensitive peripheral device 102 in order to control one or more aspects of a graphical user interface on a display associated with the computing platform 124; and/or to control one or more operational aspects of the computing platform 124. To achieve this, the user may simply apply compressive pressure to pressure sensitive peripheral device 102 by applying opposing forces to housing body 104 of the sensitive peripheral device 102. By way of non-limiting example, the one or more aspects of the graphical user interface controlled by squeezing pressure sensitive peripheral device 102 may include one or more of input of a value, selection from a menu, manipulation of a virtual object, entry of a password or a code, scrolling, moving a pointer by the user in the graphical user interface, interaction with a fitness program, interaction with a rehabilitation program, interaction with a medical treatment program, interaction with a game by the user through the graphical user interface, and/or other aspects of the graphical user interface. The one or more aspects of the computing platform controlled by the squeezing the pressure sensitive peripheral device 102 may include adjusting the volume a level of a sound output by the computing platform, turning on or off the computing platform, adjusting the resolution of a video output by the computing platform, switching between network mode (e.g., connected through Wi-Fi) or non-network mode, adjusting brightness of the display coupled to the computing platform, and/or any other operational aspects of the computing platform.

As shown, the pressure sensitive peripheral device 102 may comprise a housing body 104. The housing body 104 may be configured to house components of pressure sensitive peripheral device 102. The housing body 104 may form a shell that encloses components of pressure sensitive peripheral device 102. The housing body 104 may be a unitary body or may be comprised on two or more pieces that are joined together to form housing body 104. The housing body 104 may be made of one or more materials such as a plastic and/or other durable, semi-rigid materials suitable to form outer surfaces of pressure sensitive peripheral devices. In some implementations, pressure sensitive peripheral device 102 may include more than one housing body 104. In those implementations, the multiple housing bodies 104 may be configured to provide an open and closed configuration (e.g., the common "clamshell" design). Compressive pressure may be applied to such implementations in the closed configuration.

As shown, the pressure sensor 106 may be disposed within housing body 104. The pressure sensor 106 may be configured to provide a pressure signal conveying information associated with a compressive pressure or force applied to housing body 104 of the pressure sensitive peripheral device 102. Such information may include or be used to determine magnitude of a pressure or force, duration of a pressure or force, a pressure or force magnitude profile as a function of time, a quantity of compressive forces, and/or other information related to compressive force exerted on the housing body 104. By way of non-limiting example, pressure sensor 106 may comprise a stress gauge configured to facilitate measuring stress undergone by housing body 104, a deflection gauge configured to facilitate measuring a deflection undergone by housing body 104, and/or other devices suitable for facilitating pressure or force measurements. In some implementations, pressure sensitive peripheral device 102 may include two or more pressure sensors that are the same as or similar to pressure sensor 106. The two or more pressure sensors 106 may provide separate pressure signals, or the two or more pressure sensors 106 may provide signals that are combined into a single pressure signal.

The pressure sensor 106 may provide the pressure signal responsive to housing body 104 being squeezed by two opposing forces applied to opposing surfaces of housing body 104. The opposing forces may be applied by a user's hand, fingers, knees, and/or any other body parts of the user, and/or objects under a control of the user. For example, a user may squeeze pressure sensitive peripheral device 102 between two hands. As another example, pressure sensitive peripheral device 102 may be squeezed between a hand and a stationary surface (e.g., a tabletop). In some implementations, pressure sensitive peripheral device 102 may be configured to be removably coupled with an accessory (not depicted). The accessory may be configured to facilitate squeezing housing body 104 by two opposing forces applied to opposing surfaces of housing body 104. The accessory may include a strap, an elastic band, a stick, and/or other accessories. The accessory may include a device configured to adapt pressure sensitive peripheral device 102 to operate as a weight scale.

Examples of opposing surfaces may include a front surface and a rear surface, a top surface and a bottom surface, a left surface and a right surface, diagonally opposing surfaces, and/or other opposing surfaces of pressure sensitive peripheral device 102 (e.g., different parts of a spherical surface). In some implementations, the two opposing forces may be applied to any opposing surfaces of housing body 104. Squeezing housing body 104 by two opposing forces applied to opposing surfaces of housing body 104 does not include clicking, (e.g., clicking buttons disposed on the pressure sensitive peripheral device 102), tapping and/or dragging on a surface of the pressure sensitive peripheral device 102, or other input methods that merely require determining a presence of a physical contact (e.g., touching versus not touching a pressure sensitive pad, depressing versus not depressing a button, and/or other binary inputs). Opposing forces may be applied to entire opposing surfaces and/or portions of opposing surfaces. For example, a user may squeeze pressure sensitive peripheral device 102 using two opposing palms that cover entire opposing surfaces. As another example, a user may squeeze pressure sensitive peripheral device 102 using a thumb and index finger that contact portions of opposing surfaces.

Figure 2:
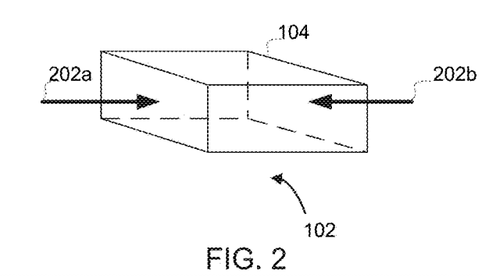
FIG. 2 illustrates one example of squeezing pressure sensitive peripheral device shown in FIG. 1 for providing inputs to a computing platform also shown in FIG. 1.

FIG. 2 illustrates one example of squeezing the pressure sensitive peripheral device shown in FIG. 1 for providing inputs to a computing platform also shown in FIG. 1. It will be described with reference to FIG. 1. As shown in this example, two opposing forces 202*a* and 202*b* may be applied to the housing body 104 of the pressure sensitive peripheral device 102 to squeeze the pressure sensitive peripheral device 102. As illustrated in this example, the two opposing forces 202*a* and 202*b* may be applied to two opposing surfaces of the housing body 104, left and right surfaces of the housing body 104 shown in this example, to squeeze the pressure sensitive peripheral device 102. However, this is not intended to be limiting. In some other examples wherein the housing body 104 is spherical or semi-spherical, it is contemplated that the opposing forces 202a and 202b may be applied to different parts of the spherical housing body 104 to squeeze the pressure sensitive peripheral device 102.

Figure 3:
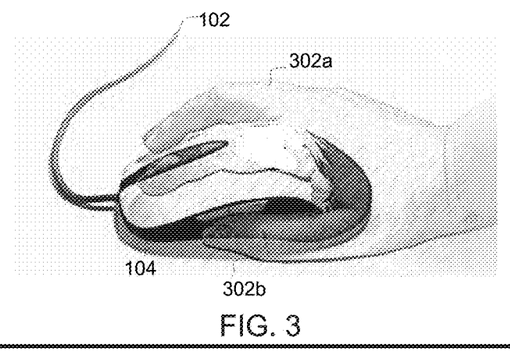
FIG. 3 illustrates one example of applying the compressive forces to the pressure sensitive peripheral device as illustrated in FIG. 2.

FIG. 3 illustrates one example of applying the compressive forces to the pressure sensitive peripheral device as illustrated in FIG. 2. It will be described with reference to FIGS. 1-2. As shown in this example, a user may squeeze the pressure sensitive peripheral device 102 (i.e., a pressure sensitive mouse 102 in this example) to apply the compressive forces illustrated in FIG. 2. As illustrated, a user may squeeze the pressure sensitive mouse 102 with fingers 302a and 302b to provide inputs to the computing platform 104.

Returning to FIG. 1, in some implementations, pressure sensor 106 may be configured to provide multiple pressure signals conveying information associated with multiple forces applied to housing body 104. Individual ones of the multiple pressure signals may be provided responsive to housing body 104 being squeezed multiple of forces applied to multiple sets of opposing surfaces of housing body 104, or multiple parts of the surface of housing body 104. In those implementations, the pressure sensors may be configured to provide contemporaneous or near-contemporaneous pressure signals in response to the multiple forces squeezing the housing body 104.

Figure 4:
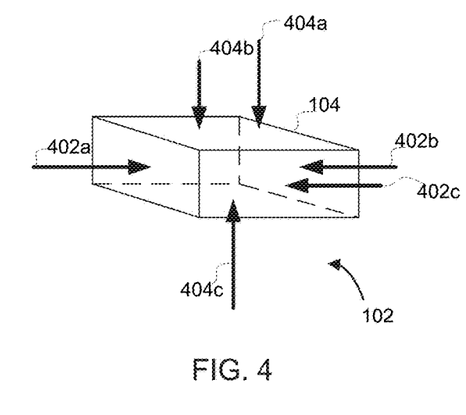
FIG. 4 illustrates one example of the housing body of a pressure sensitive peripheral device shown in FIG. 1 being squeezed by multiple forces.

FIG. 4 illustrates one example of the housing body of a pressure sensitive peripheral device shown in FIG. 1 being squeezed by multiple forces. It will be described with reference to FIG. 1. As shown in this example, the housing body 104 of the pressure sensitive peripheral device 102 may be squeezed by a first set of forces 402A-402C on the left and right surfaces of the housing body 104. As illustrated in FIG. 4, multiple forces (e.g., force 402B and 402C shown in FIG. 4) may be applied on any one of the surface. As described above, the pressure sensor 106 disposed within the housing body 104 may provide contemporaneous pressure signals to convey information indicating multiple pressures on the housing body 104 as a result of the first set of forces 402A-C.

Also shown in FIG. 4 is a second set of forces 404A-D applied to the top and bottom surfaces of the housing body 104 of the pressure sensitive peripheral device 102. This illustrates multiple forces 404A-C may be applied simultaneously or near simultaneously with the first set of forces 402A-C to squeeze the housing body 104 on different surfaces. The pressure sensor 106 within the housing body 104 is configured, in this example, to provide pressure signals conveying information about the multiple forces 404A-C, in addition to providing the pressure signals conveying information about the first set of forces 402A-C. This may be achieved by disposing multiple pressure sensors 106 within the housing body 104 for detecting compressive forces exerted on different sets of opposing surfaces of the housing body 104. However, it should be understood, in some other examples, a single pressure sensor 106 may be employed in the pressure sensitive peripheral device 102 for detecting the multiple compressive forces exerted on the multiple sets of the compressive forces. In those examples, the pressure sensor 106 may output a single pressure signal at a given time point with encoded information regarding the multiple compressive forces.

Figure 5:
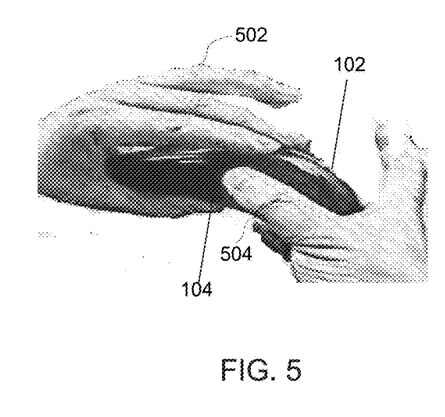
FIG. 5 illustrates one example of applying the compressive forces to the pressure sensitive peripheral device as illustrated in FIG. 4.

FIG. 5 illustrates one example of applying the compressive forces to the pressure sensitive peripheral device as illustrated in FIG. 4. It will be described with reference to FIG. 4. As illustrated in FIG. 4, a user may use left hand fingers 502 to squeeze the top and bottom surfaces of the housing body 104 of the pressure sensitive mouse 102 shown in FIG. 5 to exert forces 404A-C as shown in FIG. 4. As also illustrated in FIG. 4, the user may simultaneously use right hand fingers 504 to squeeze the right and left surfaces of the housing body 104 to exert forces 402A-C as shown in FIG. 4. As described above, responsive to such squeezing of the housing body 104 by the user, the pressure sensor 106 within the pressure sensitive mouse 102 may provide pressure signal(s) to convey information regarding the multiple compressive forces, 402A-C and 404A-C, exerted on the housing body 104 of the pressure sensitive mouse 102. As described below, the squeezing of the pressure sensitive mouse 102 shown in FIG. 5 may enable the user to perform isometric fitness routine(s) to interact with a fitness program, rehabilitation program, treatment program and/or other programs on the computing platform 124.

Returning to FIG. 1, in some examples, the pressure sensor 106 may be configured such that a pressure signal regarding compressive forces on two opposing surfaces may be provided only when the compressive forces has breached certain threshold. For example, to achieve this, the pressure sensor 106 may measure the compressive forces and compare the measured forces with a threshold pressure value preconfigured with the pressure sensor 106 or with the pressure sensitive peripheral device 102. In that example, the pressure signal may be provided by the pressure sensor 106 only when the comparison indicates the measured compressive forces is greater than the threshold pressure value.

In some implementations, the pressure sensitive peripheral device 102 may include a vibration sensor 108. The vibration sensor 108 may be configured to provide a vibration signal conveying information regarding a vibration of the pressure sensitive peripheral device 102. The information conveyed by the vibration signal may include a rate of vibration, a magnitude of the vibration, directions of the vibration, and/or any other information regarding the vibration of the pressure sensitive peripheral device 102.

In some implementations, the pressure sensitive peripheral device 102 may include an accelerometer 110. The accelerometer 110 may provide rotation signals conveying information regarding a ration of the pressure sensitive peripheral device 102. For example, the accelerometer 110 may include a tilt sensor (not depicted) to detect a rotation of the pressure sensitive peripheral device 102. The information conveyed by the rotation signals may include a direction of the rotation, a degree of the rotation, a rate of the rotation, and/or any other rotation information regarding the pressure sensitive peripheral device 102.

In some implementations, the pressure sensitive peripheral device 102 may include a heart rate sensor 112. The heart rate sensor 112 may be configured to provide a heart rate output signal that conveys information related to a heart rate of a user associated with pressure sensitive peripheral device 102. The heart rate sensor 118 may utilize electrocardiography (ECG or EKG). The heart rate output signal may be used to monitor heart rate in real time or record heart rate data for later observation and/or analysis. In some implementations, heart rate sensor 112 is integrated into pressure sensitive peripheral device 102 such that heart rate sensor 112 may measure a user's heart rate by way of physical contact between the user and pressure sensitive peripheral device 102. The heart rate sensor 112 may communicatively couple with a heart rate monitor that is separate and distinct from pressure sensitive peripheral device 102, according to some implementations. Examples of separate and distinct heart rate monitors may include a chest strap, a finger clip, a garment with an integrated heart rate monitor, and/or other devices configured to probe heart rate.

In some implementations, the pressure sensitive peripheral device 102 may include a blood pressure sensor 114. The blood pressure sensor 114 may be configured to generate a blood pressure output signal that conveys information related to a blood pressure of a user associated with pressure sensitive peripheral device 102. The blood pressure sensor 114 may be based on one or more non-invasive technologies including near IR detection, ultrasound, dielectric spectroscopy, and/or other non-invasive technologies for determining glucose concentration, in accordance with some implementations.

Other component sensors, although not shown in FIG. 1, may be included in the pressure sensitive peripheral device 102. For example, in one implementation, the pressure sensitive peripheral device 102 includes a motion sensor for providing motion signals conveying information related to motion and/or orientation of the pressure sensitive peripheral device 102. In another implementation, the pressure sensitive peripheral device includes pedometer conveying information related to a number of steps taken by the user of the pressure sensitive peripheral device 102.

In some implementations, the pressure sensitive peripheral device 102 may include a user interface 116. The user interface 116 may include a touch sensitive surface, one or more buttons, a touch pad, a touch pointer, and any other types of user interface that may be suitably provided on housing body 104 of the pressure sensitive peripheral device 102. The user interface 116 may be configured to receive user inputs for controlling the pressure sensitive peripheral device 102 and/or as well as the computing platform 124. In some implementations, the control inputs received from the user interface 116 may be separate and independent from the inputs received from the pressure sensor 106; and in some other implementations, the control inputs received from the user interface 116 may augment the inputs received from the pressure sensor 106. For example, in one implementation, a user may be enabled to select a type of compressive forces to be applied by the user on the housing body 104 of the pressure sensitive peripheral device 102 (e.g., squeezing the pressure sensitive peripheral device 102 from the side) through a touch sensitive interface 118 and applying the selected compressive forces to the pressure sensitive peripheral device 104. In that implementation, the user interface 116 may be configured to provide the user selection of the type of compressive forces being applied by the user to the pressure sensor 106 and/or electronic circuitry 118. In this way, the pressure applied by the user may be more accurately measured and determined.

In some implementations, the pressure sensitive peripheral device 102 may include electronic circuitry 118. The electronic circuitry 118 may be configured to provide signal processing capabilities in pressure sensitive peripheral device 102. As such, electronic circuitry 118 may include one or more of a digital processor, an analog processor, a digital circuit designed to process information, an analog circuit designed to process information, a state machine, and/or other mechanisms for electronically processing information. The electronic circuitry 118 may be configured to process pressure signals provided by the pressure sensor 106 and other signals provided by other sensors described above and herein. The electronic circuitry 118 may be configured to generate and provide control inputs to the computing platform 124 based on the received signals. As illustrated, to achieve these functionalities, the electronic circuitry 118 may include a signal component, an input provision component, and/or any other component(s).

Although electronic circuitry 118 is shown in FIG. 1 as a single entity, this is for illustrative purposes only. In some implementations, electronic circuitry 118 may include a plurality of processing units. These processing units may be physically located within the same device, or electronic circuitry 118 may represent processing functionality of a plurality of devices operating in coordination. The electronic circuitry 118 may be configured to execute components 120, 122, and/or other components. The electronic circuitry 118 may be configured to execute modules 120, 122, and/or other modules by software, hardware, firmware, some combination of software, hardware, and/or firmware, and/or other mechanisms for configuring processing capabilities on electronic circuitry 118. As used herein, the term "component" may refer to any component or set of components that perform the functionality attributed to the module. This may include one or more physical processors during execution of processor readable instructions, the processor readable instructions, circuitry, hardware, storage media, or any other components.

It should be understood that, although modules 120 and 122 are illustrated in FIG. 1 as being implemented within a single processing unit, in implementations in which processor(s) 124 includes multiple processing units, one or more of modules 120 and/or 122 may be implemented remotely from the other modules. The description of the functionality provided by the different modules 120 and/or 122 described below is for illustrative purposes and is not intended to be limiting, as any of modules 120 and/or 122 may provide more or less functionality than is described. For example, one or more of modules 120 and/or 122 may be eliminated and some or all of its functionality may be provided by other ones of modules 120 and/or 122. As another example, processor(s) 124 may be configured to execute one or more additional modules that may perform some or all of the functionality attributed below to one of modules 120 and/or 122.

The signal component 120 may be configured to receive pressure signals provided by the pressure sensors and as well as signals provided by other sensors described above and herein if they are included in the pressure sensitive peripheral device 102. To achieve this, the signal component 120 may include timing circuitry configured to poll the pressure signals and other signals (if provided) periodically. In some implementations, the signal component 120 may poll one or more registers for receiving the signals. By way of non-limiting example, a register may be provided within the electronic circuitry 118 such that the pressure sensor 106 may provide the pressure signals by storing data indicating the pressure signal in the register whenever the squeezing of the pressure sensitive peripheral device 102 is detected and measured by the pressure sensor 106. In that example, the signal component 120 may poll the register for receiving the pressure signals from the pressure sensor 106 periodically (e.g., once every $\frac{1}{10}$th of a second). In some other implementations, the signal component 120 may include circuitry that facilitates interrupts such that an interrupt may be generated when a pressure signal is provided by the pressure sensor 106.

The signal component 120 may be configured to process the pressure signals and other signals (if provided). The signal processing by the signal component 120 may include modulation, amplification, decoding, encoding, noise cancelling, and/or any other types of signal processing operations that may be performed by the signal component 120. By way of non-limiting example, in one implementation, the pressure signals provided by the pressure sensor 106 may be in an analog format (e.g., a voltage profile). In that implementation, the signal component 120 may modulate the signals and detect sudden increase of the voltage as indicated by the pressure signals provided by the pressure sensor 106 for determining corresponding compressive forces applied to the pressure sensitive peripheral device 102 (e.g., squeezing of the pressure sensitive peripheral device 102 by a user) that caused the voltage increase. In that example, a table of voltage and compressive force correlation may be stored within the electronic circuitry 118 (e.g., inside a memory chip); and during runtime of the pressure sensitive peripheral device 102, the signal component 120 may consult such a table for determining an amount of pressure/force that caused the increase of the voltage as indicated by the pressure sensor 106.

In some implementations, the pressures signals and other signals (if provided) may be digitally encoded to represent corresponding information conveying corresponding actions/changes to the pressure sensitive peripheral device 102 detected. In those implementations, the signal component 120 may be configured to decode the digitally encoded information. By way of non-limiting example, the pressure signals provided by the pressure sensor 106 may be digitally encoded to represent an amount of pressure/force detected or measured by the pressure sensor 106. For instance, a "0010" may mean that 4 pounds of force was measured by the pressure sensor 106 as a result of squeezing of the pressure sensitive peripheral device 102 by a user; a "0011" may mean that 5 pounds of force was measured by the pressure sensor 106 as a result of squeezing of the pressure sensitive peripheral device 102 by a user; and so on. In those implementations, a table of digital code and amount of pressure/force correlation may be stored within the electronic circuitry 118 (e.g., inside a memory chip). During runtime of the pressure sensitive peripheral device 102, the signal component 120 may consult such a table to decode pressure signals and as well as other signals (if provided).

In some implementations, the signal component 120 may be configured to receive multiple contemporaneous pressure signals provided by pressure sensor 106. In those implementations, the signal component 120 may be configured to interpret the multiple contemporaneous pressure signals to control one or more aspects of operation of the computing platform 124.

The input provision component 122 may be configured to provide an input to the computing platform 124 based on the received pressures signals for controlling one or more aspects of the computing platform 124. The one or more aspects may be related a graphical user interface on a display associated with the computing platform 124 and/or operational aspects of the computing platform 124. Providing inputs based on the received pressure signals may include generating the inputs as a function of the pressure/force detected or measured by the pressure sensor 106 as indicated by the received signals. By way of non-limiting example, the input provision component 122 may be configured to generate a binary signal for controlling a graphical user interface based on whether the pressure/force indicated by the received pressure signals has breached certain threshold value. For instance, the threshold value may be set as 5 pounds of force, and the control input provision component 122 may generate a signal (e.g., a signal indicating "trigger pressed" by a user for initiating a game action in a game running on the computing platform 124) only if the user has squeezed the pressure sensitive peripheral device 120 (for example as illustrated in FIG. 3) with compressive forces greater than 5 pounds.

It should be understood that an input provided by the input provision component 122 to the computing platform 124 based on the pressure signal may be an analog value or a digital value. Digital values having very fine granularity may be interpreted by a user as quasi-analog input. By way of non-limiting example, a user may squeeze the pressure sensitive peripheral device 102 with varying forces in order to enter a value on a quasi-analog meter presented on the display where smaller forces correspond to smaller values on the meter and larger forces correspond to larger values on the meter. In that example, the control input provision component 122 is configured to generate control input correlating the amount of pressure/force applied to the housing body 104 as a result of the squeezing of the pressure sensitive peripheral device 102 by the user. For instance, an input of "1" may be generated if one pound of force is detected, an input of "2" may be generated if two pounds of force is detected, an input of "3" may be generated if three pounds of force is detected and so on. As another example, a user may enter a height of the user in a text field presented on the display where smaller forces correspond to shorter heights and larger forces correspond to taller heights. However, in some examples, the control inputs provided to the computing platform 124 may be in analog format. For example, the input provision component 122 may provide continuous analog inputs corresponding to the varying forces applied to the housing body 104 by the user to computing platform 124. Such analog inputs may be useful for interacting with a fitness program that instructs a user to perform isometric exercise routine.

In some implementations, the input provision component 122 may be configured to interpret the received pressure signal to control one or more aspects of operation of pressure sensitive peripheral device 102 based on a position on pressure sensitive peripheral device 102 on which the opposing forces were applied. By way of non-limiting example, squeezing front and rear surfaces of pressure sensitive peripheral device 102 may correspond to one input, while squeezing top and bottom surfaces of pressure sensitive peripheral device 102 may correspond to another input.

In some implementations, the control input provision component 122 may be configured to quantify the compressive pressure applied to housing body 104. For example, the input provision component 122 may quantify the compressive pressure applied to housing body 104 on an arbitrary scale such as a scale between one and ten, a scale between one and five stars, and/or other arbitrary scale. As another example, the control input provision component 122 may quantify the compressive pressure or force (or other suitable metric) applied to housing body 104 in absolute units such as pounds (lb), kilograms (kg), Newtons (N), pounds per square inch (PSI), Pascals (Pa), Newtons per meters squared (N/m$^2$), and/or other absolute units.

Figure 6:
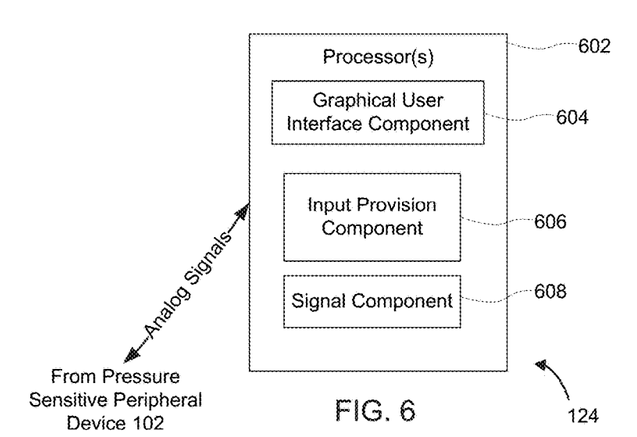
FIG. 6 illustrates one example of computing platform 124 shown in FIG. 1 for facilitating receiving user inputs from a pressure sensitive peripheral device.

As illustrated in FIG. 1, the pressure sensitive peripheral device 102 may be configured to communication with one or more computing platforms 124 (e.g., one or more servers 116 and/or one or more computing platforms 118) via any suitable wired or wireless communication medium, such as, but not limited to, universal serial bus (USB), coaxial cable, Bluetooth, near field radio frequency, or any other types of wired or wireless communication medium. As illustrated, the pressure sensitive peripheral device 102 may provide inputs and/or signals to the computing platform 124 for controlling one or more aspects of the computing platform 124. As described above and herein, in some implementations, the pressure sensitive peripheral device 102 may include electronic circuitry, such as the electronic circuitry 118 described above and herein, configured to provide inputs to the computing platform 124 based on the pressure signals and any other signals (if provided). However, this is not necessarily the only case. In some implementations, some or all of the functionality attributed to the electronic circuitry 118 described above and herein may reside within the computing platform 124. For example, in one implementation, one or more driver components may be included in the computing platform 124 for receiving and processing the control signals from the pressure sensitive peripheral device 102. In that implementation, the pressure sensitive peripheral device 102 may be configured to transmit analog signals conveying magnitude of the compressive forces applied to the housing body 104 at any given point of time, and the driver component(s) on the computing platform 124 may be configured to receive and interpret the analog pressure signals and generate control inputs based on the received signals in the similarly way(s) to that described above for electronic circuitry 122. FIG. 6 illustrates one example of such an implementation. As illustrated in FIG. 6, one or more processors 602 of the computing platform 124 may comprise a signal component 608 with the similar or same functionalities to those attributed to signal component 122 (described above and herein), a input provision component 606 with the similar or same functionalities to those attributed to input provision component 120 (described above and herein), and/or any other driver components. As also shown in FIG. 6, the processor(s) 602 may include a graphical user interface component that provides graphical user interface for a user to interact with the computing platform 124.

Returning to FIG. 1, the inputs to the computing platform 124 based on pressure signals provided by the pressure sensor 106 may be used to control one or more aspects of the computing platform 124. The one or more aspects may include one or more aspects of a graphical user interface on a display associated with the computing platform 124, one or more operational aspects associated of the computing platform 124, and/or any other aspects of the computing platform 124. By way of non-limiting example, the one or more aspects of the graphical user interface controlled by squeezing pressure sensitive peripheral device 102 may include one or more of input of a value, selection from a menu, manipulation of a virtual object, entry of a password or a code, scrolling, moving a pointer by the user in the graphical user interface, interaction with a fitness program, interaction with a rehabilitation program, interaction with a medical treatment program, interaction with a game by the user through the graphical user interface, and/or other aspects of the graphical user interface on the display associated with pressure sensitive peripheral device 102. Some aspects of the graphical user interface that may be controlled by squeezing the pressure sensitive peripheral device 102 are described below. It should be understood that these descriptions are illustrative and thus not intended to be limiting or exhaustive. One skilled in the art will appreciate other input methods enabled by squeezing the pressure sensitive peripheral device 102 in accordance with the present disclosure.

Input of a value such as a password through the pressure sensitive peripheral device 102 may be achieved by a sequence of squeezes performed on pressure sensitive peripheral device 102. For example, a user may perform different magnitudes and/or different durations of squeezes on pressure sensitive peripheral device 102. For instance, a user may perform a specific combination of short and long squeezes on pressure sensitive peripheral device 102 as a password input to the computing platform 124 via the graphical user interface. Combinations of squeezes on different locations of pressure sensitive peripheral device 102 may be used as input of different values, according to some implementations.

Selection from a menu in the graphical user interface through the pressure sensitive peripheral device 102 may be achieved by a squeeze with compressive force within a range corresponding to a menu item in the menu. By way of non-limiting example, a user may be enabled to select different menu items from the menu by squeezing the pressure sensitive peripheral device 102 with varying compressive forces. For instance, a first menu item may be selected by the user by squeezing the pressure sensitive peripheral device 102 with a first range of compressive forces (e.g., 1-3 pounds), a second menu item may be selected by the user by squeezing the pressure sensitive peripheral device 102 with a second range of compressive forces (e.g., 3-5 pounds), a third menu item may be selected by the user by squeezing the pressure sensitive peripheral device 102 with a third range of compressive forces (e.g., 5-7 pounds), and so on. However, this is not intended to be limiting. In some implementations, selection of menu items may be achieved by squeezing the pressure sensitive peripheral device 102 at different surfaces or locations (if the surface of the pressure sensitive peripheral device is spherical).

Scrolling the graphical user interface on the display associated with the computing platform 124 may be achieved by squeezing the pressure sensitive peripheral device 102 with compressive forces intermittently with more or less a uniform cadence. By way of non-limiting example, a user may be enabled to scroll the graphical user interface by squeezing the pressure sensitive peripheral device 102 in an on-and-off manner repetitively. The direction of scrolling may be achieved by squeezing different parts of the pressure sensitive peripheral device 102. For instance, squeezing front part of side surfaces of housing body 104 of a pressure sensitive mouse 102 may enable the user to scroll the graphical user interface up; and squeezing the rear part of the side surfaces of the pressure sensitive mouse 102 may enable the user to scroll the graphical user interface down.

Manipulation of a virtual object based on the pressure signal may be further based on an accelerometer signal conveying a position and/or a change in position of pressure sensitive peripheral device 102. For example, a virtual object may be "grasped" by squeezing pressure sensitive peripheral device 102. The position of the virtual object may be controlled through corresponding a position and/or a change in position of pressure sensitive peripheral device 102. The accelerometer signal may be provided by an accelerometer (not depicted) and/or other position detection device included in pressure sensitive peripheral device 102. In one implementation, exertion and release of pressure may respectively result in zoom-in and zoom-out of a three-dimensional virtual space.

Interaction with a fitness program through the graphical user interface by the user may include squeezing pressure sensitive peripheral device 102 by the user. The pressure signals provided by the pressure sensor 106 as a result of the user squeezing of the pressure sensitive peripheral device 102 may be used during isometric and/or dynamic exercise routines in the fitness program, such as those disclosed in U.S. patent application Ser. No. 13/527,465 filed on Jun. 19, 2012 and entitled "Personal Wellness Device," which is incorporated herein by reference. Such routines may be provided by the fitness program, which may involve user squeezing pressure sensitive peripheral device with a threshold force, for a threshold duration of time, for a number of repetitions, and/or other exercise metrics. According to some implementations, the fitness program may include squeezing pressure sensitive peripheral device 102 to achieve a variable target force over time. For example, a graphical indication and/or other indication may convey, via the graphical user interface, to a user when the force applied is above or below a target force. The target force may change over time, according to a fitness program. The target force may change responsive to the applied force equaling the target force.

By way of non-limiting example, the fitness program may include elements instructing or challenging a user to perform a isometric exercise routine, including but not limited to, squeezing the pressure sensitive peripheral device 102 using two hands for certain duration. In that example, the user may be enabled to perform such an isometric routine as illustrated by FIG. 5. Upon successful performance of the isometric exercise routine by the user, the fitness program may reward the user with virtual points, currency, unlocking of virtual items, new exercise routine(s), and/or other types of rewards. In some instances, the fitness program may instruct the user to perform the isometric exercise route in a corrected form upon interpreting the squeezing motion conveyed by the pressure signals provided by the pressure sensor 106. In those implementations, the fitness program may include analysis component that analyzes user performance of isometric exerciser routines facilitated by the fitness program. In some implementations, the fitness program may instruct, challenge or otherwise motivate a user to squeeze the pressure sensitive peripheral device 102 while moving the pressure sensitive peripheral device 102 along a predetermined curve line. In those implementations, the pressure sensitive peripheral device 102, such as a pressure sensitive mouse 102, may provide signals indicating pressure applied by the user on the housing body of the pressure sensitive mouse 102, motion performed by the pressure sensitive mouse 102, and any other information.

Figure 7:
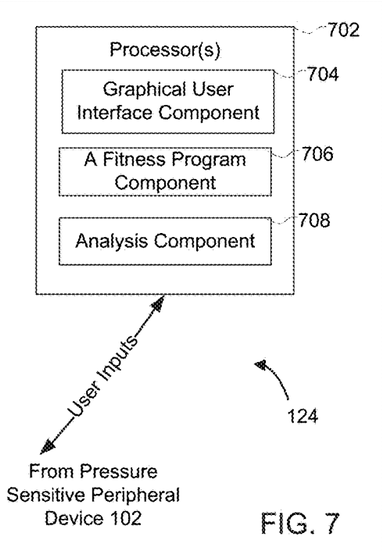
FIG. 7 illustrates another example of computing platform 124 shown in FIG. 1 for facilitating receiving user inputs from a pressure sensitive peripheral device.

FIG. 7 illustrates one example of computing platform 124 for facilitating receiving user inputs from a pressure sensitive peripheral device 102. It will be described with reference to FIG. 1. In this example, the processor(s) 702 of the computing platform 124 is configured with a graphical user interface component 704, a fitness program component 706, an analysis component 708, and other components. As shown, the computing platform 124 may receive user inputs from the pressure sensitive peripheral device 102. The received user inputs may include information indicating performance of an isometric routine (e.g., squeezing the pressure sensitive peripheral device 102 with certain compressive forces for a certain duration). The analysis component 708 may be configured to analyze the performance of the isometric exercise by the user based on the received user inputs. The fitness program 706 may be configured to provide the user instructions, challenges, rewards, aids, and/or any other types of elements to engage the user to perform isometric exercise routines and/or any other types of exercise routines. The graphical user interface component 704 may be configured to provide graphical indications, visual cues, instructions, and/or any other types of feedbacks to the user regarding their performance of isometric exercises routines, instructions, challenges, and/or any other types of feedbacks.

Interaction with a game through the pressure sensitive peripheral device 102 may include user squeezing the pressure sensitive peripheral device 102 to initiate one or more game actions in the game. The game actions enabled by the pressure sensitive peripheral device 102 may include movement with a force (e.g., thrusting, dashing, turbo charge, etc.), combat action with a force (e.g., jabbing, heaving, waving with a corresponding force, etc.), firing a shot, changing camera angles, selecting next weapon, accelerating, looking around, changing virtual character/units/avatar under control, and/or any other game actions.

By way of non-limiting example, a user may be enabled to initiate a game action such as punching, thrusting, heaving, waving, or any other hand movements of a virtual character (e.g., an avatar representing the user) with varying forces. For instance, the user may be enabled to initiate such an action with little force by squeezing the pressure sensitive peripheral device 102 lightly, and to initiate such an action with much force by squeezing the pressure sensitive peripheral device 102 strongly. In one implementation, the pressure sensitive peripheral device 102 is a pressure sensitive mouse; and in that implementation, the user is enabled to initiate n combat action with varying forces by controlling the compressive forces applied to the housing body 104 of the pressure sensitive mouse 102. In another example, the pressure sensitive peripheral device 102 is a pressure sensitive joystick; and in that implementation, the user is enabled to initiate a movement in the game with varying forces by squeezing the pressure sensitive joystick 102 with varying compressive forces while moving the pressure sensitive joystick 102 directionally.

By way of another non-limiting example, the user may be enabled to initiate an aim and shoot action in the game by squeezing the pressure sensitive peripheral device 102 with compressive forces above certain threshold value. This may simulate a trigger action. In some examples, the user may be enabled to select next weapon in the game by repetitively squeeze the pressure sensitive peripheral device 102 until a desired weapon is selected by the user. Still in another example, the user may be enabled to accelerate a virtual vehicle under control of the user in the game by squeezing the pressure sensitive peripheral device 102 suddenly. It should be understood these are just some of the game controls that may be achieved by squeezing the pressure sensitive peripheral device 102 for illustration purpose. Accordingly, these examples are not intended to be limiting or exhaustive. One skilled in the art will appreciate other examples of game controls enabled by squeezing the pressure sensitive peripheral device 102 in accordance with the disclosure.

Figure 8:
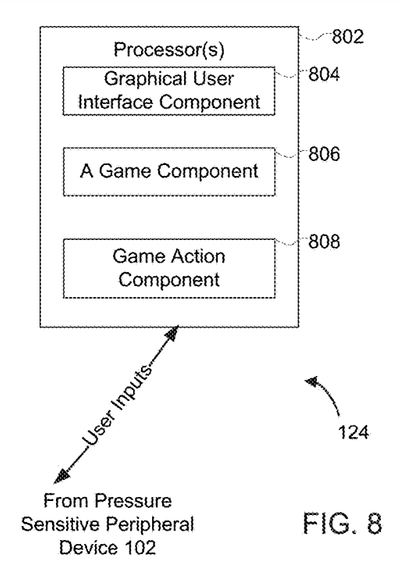
FIG. 8 illustrates yet another example of computing platform 124 shown in FIG. 1 for facilitating receiving user inputs from a pressure sensitive peripheral device also shown in FIG. 1.

FIG. 8 illustrates yet another example of computing platform 124 shown in FIG. 1 for facilitating receiving user inputs from a pressure sensitive peripheral device also shown in FIG. 1. In this example, the processor(s) 802 of the computing platform 124 is configured with a graphical user interface component 804, a game component 806, a game action component 808, and other components. As shown, the computing platform 124 may receive user inputs from the pressure sensitive peripheral device 102. The received user inputs that initiate one or more game actions in the game provided by the game component 808 (e.g., by squeezing the pressure sensitive peripheral device 102 with certain compressive forces for a certain duration). The game action component 808 may be configured to interpret the user inputs received from the pressure sensitive peripheral device 102. The game action component may translate the received user inputs into one or more corresponding game actions as predefined by a provider, administrator, moderator, and/or any other entities related to the game provided by the game component 806. The fitness program 806 may be configured to provide the game by determining one or more states of the game at a given time point. Determining the game state(s) by the game component may include determining a result of the game action(s) initiated by the user through squeezing the pressure sensitive peripheral device 102. The graphical user interface component 804 may be configured to provide an interface for user to interact with the game provided by the game component 806. The interface provided by the graphical user interface component 804 may include views of the game to reflect the result of the game action(s) initiated by the user through squeezing the pressure sensitive peripheral device 102.

Figure 9:
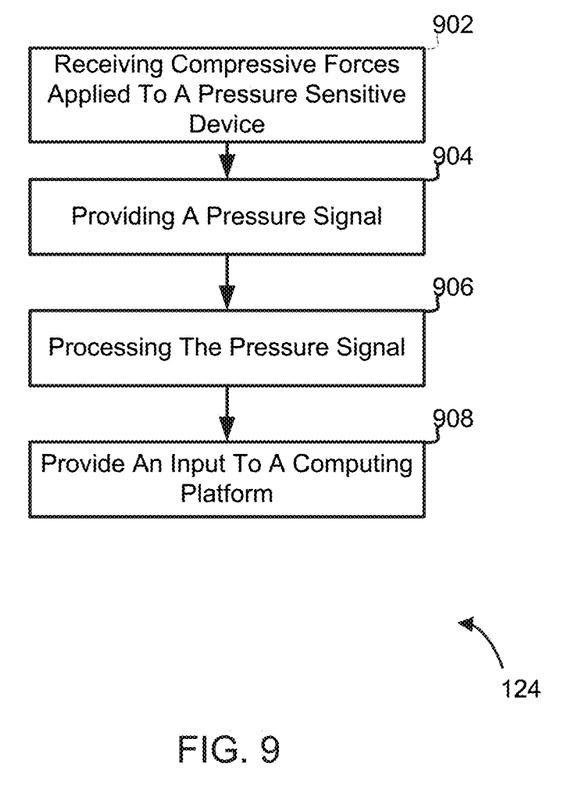
FIG. 9 illustrates an exemplary method of facilitating receipt of user input using a pressure sensitive peripheral device with a pressure sensor in accordance with the disclosure.

FIG. 9 illustrates a method 900 of facilitating receipt of user input using a pressure sensitive peripheral device with a pressure sensor in accordance with the disclosure. The operations of method 900 presented below are intended to be illustrative. In some embodiments, method 900 may be accomplished with one or more additional operations not described, and/or without one or more of the operations discussed. Additionally, the order in which the operations of method 900 are illustrated in FIG. 9 and described below is not intended to be limiting.

In some embodiments, method 900 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

At an operation 902, compressive forces applied to a housing body or housing bodies of a pressure sensitive peripheral device may be received. In some implementations, the compressive forces received in operation 902 may be applied by a user to any opposing surfaces of housing body of pressure sensitive peripheral device, i.e. squeezing the pressure sensitive peripheral device. This does not include clicking, (e.g., clicking buttons disposed on the pressure sensitive peripheral device 102), tapping and/or dragging on a surface of the pressure sensitive peripheral device 102, or other input methods that merely require force in one direction instead of two opposing forces applied to two opposing surfaces. A user may squeeze pressure sensitive peripheral device using two opposing palms that cover entire opposing surfaces. As another example, a user may squeeze pressure sensitive peripheral device using a thumb and index finger that contact portions of opposing surfaces. In some implementations, multiple compressive forces applied to different surfaces or parts of the housing body of the pressure sensitive peripheral device may be received in operation 902. In some implementations, operation 902 may be performed by one or more of a pressure sensor disposed within the housing body or bodies of the pressure sensitive peripheral device that is the same as or similar to the pressure sensor 106 described above and herein.

At an operation 904, a pressure signal based on the compressive forces received in operation 902 may be provided. The pressure signal provided by operation 904 may convey information associated with the compressive forces received in operation 902. The information may include a magnitude of a pressure or force, duration of a pressure or force, a pressure or force magnitude profile as a function of time, a quantity of compressive forces, and/or other information related to compressive force applied on the housing body or housing bodies of the pressure sensitive peripheral device. In some implementations, operation 904 may be performed by one or more of a pressure sensor disposed within the housing body or bodies of the pressure sensitive peripheral device that is the same as or similar to the pressure sensor 106 described above and herein.

In operation 906, the signal provided in operation 904 may be processed. Processing the signal in operation 906 may involve modulation, amplification, decoding, encoding, noise cancelling, and/or any other types of signal processing operations that may be performed to process the signal from the pressure sensor. In some implementations processing the signal in operation 906 may include quantify a pressure or force indicated by the signal on an absolute and/or arbitrary scale. In some implementations, the signal from the pressure sensor may indicate multiple forces applied to different surfaces or parts of the pressure sensitive peripheral device contemporaneously or near contemporaneously. In those examples, operation 906 may interpret the multiple forces for providing inputs. In some implementations, operation 904 may be performed by a signal component that is the same as or similar to the signal component 120 described above and herein.

In operation 908, an input to a computing platform may be provided based on the signal processing in operation 906. The input provided in operation 908 may be used to control one or more aspects of the computing platform, which may include one or more aspects of a graphical user interface on a display associated with the computing platform, one or more operational aspects of the computing platform, and/or any other aspects of the computing platform. By way of non-limiting example, the one or more aspects of the graphical user interface may include one or more of input of a value, selection from a menu, scrolling, moving a pointer, manipulation of a virtual object, entry of a password or a code by the user in the graphical user interface, interaction with a fitness program, interaction with a rehabilitation program, interaction with a medical treatment program, interaction with a game by the user through the graphical user interface, and/or other aspects of the graphical user interface. The one or more operational aspects of the computing platform may including volume a level of a sound output by the computing platform, powering on or off the computing platform, resolution of a video output by the computing platform, network mode (e.g., connected through Wi-Fi) or non-network mode (e.g., no network connections), brightness of a display coupled to the computing platform, and/or any other operational aspects of the computing platform. In some implementations, operation 908 may be performed by an input provision component that is the same as or similar to the input provision component 122 described above and herein.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A pressure sensitive peripheral device with one or more pressure sensors to facilitate receipt of user inputs to a computing platform, the pressure sensitive peripheral device comprising:
   a housing body;
   one or more pressure sensors disposed within and in contact with the housing body, the one or more pressure sensors being configured to provide a pressure signal conveying information from a compressive pressure applied to the housing body, the pressure signal being provided responsive a first set of two opposing forces applied to the housing body, wherein the first set of two opposing forces does not perform a clicking motion; and,
   wherein the one or more pressure sensors are further configured to transmit the pressure signal to electronic circuitry configured to:
      receive the pressure signal provided by the one or more pressure sensors, and
      responsive to receiving the pressure signal provided by the one or more pressure sensors, provide an input to the computing platform based on the received the pressure signal which is constant or variable in time, the input being provided to facilitate controlling a graphical user interface presented on a display associated with the computing platform in accordance with a fitness exercise shown by the graphical user interface,
      wherein providing the input to the computing platform based on the received pressure signal provided by the one or more pressure sensors comprises determining whether the compressive pressure applied to the housing body has reached a minimum magnitude that corresponds to a minimum physical exercise level, and only providing the input to the computing platform responsive to the compressive pressure reaching the minimum magnitude, wherein controlling the graphical user interface in accordance with the fitness exercise includes movement of an indicator shown by the graphical user interface by compressing the housing body of the pressure sensitive peripheral device such that the indicator moves along a curve line displayed by the graphical user interface for a time period.

2. The pressure sensitive peripheral device of claim 1, wherein the one or more pressure sensors are further configured to provide a second pressure signal conveying information associated with a second compressive pressure applied to the housing body, the second pressure signal being provided responsive to a second set of two opposing forces applied to parts of the housing body, wherein the second set of two opposing forces are separate and discrete from the first set of two opposing forces.

3. The pressure sensitive peripheral device of claim 1, wherein the electronic circuitry is further configured such that providing the input to the computing platform based on the received pressure signal provided by the one or more pressure sensors comprises determining whether the compressive pressure applied to the housing body has breached a threshold minimum magnitude level that corresponds to the minimum physical exercise level.

4. The pressure sensitive peripheral device of claim 1, wherein controlling the graphical user interface presented on the display associated with the computing platform as facilitated by the provided input also includes one or more of:
   input of a value in the graphical user interface;
   selection from a menu in the graphical user interface;
   scrolling the graphical user interface;
   moving a pointer in the graphical user interface;
   manipulation of a virtual object in the graphical user interface;
   entry of a password or a code in the graphical user interface;
   interaction with a rehabilitation program through the graphical user interface;
   interaction with a medical treatment program through the graphical user interface; and
   interaction with a game through the graphical user interface.

5. The pressure sensitive peripheral device of claim 1, wherein the fitness exercise is an isometric exercise.

6. The pressure sensitive peripheral device of claim 1, wherein controlling the graphical user interface in accordance with the fitness exercise includes compression of the pressure sensitive peripheral device with a threshold force, for a threshold duration of time, and/or for a number of repetitions.

7. The pressure sensitive position device of claim 4, wherein interaction with the game includes performing one or more game actions through the pressure sensitive peripheral device.

8. The pressure sensitive peripheral device of claim 4, wherein entry of the password or the code based on the pressure signal is achieved by a sequence of forces applied on the pressure sensitive peripheral device, a rotation of the pressure sensitive peripheral device, and/or one or more gestures input through display associated with the computing platform.

9. The pressure sensitive peripheral device of claim 1, further comprising an accelerometer and/or a gyroscope configured to provide a position signal conveying a position and/or a change in position of the pressure sensitive peripheral device, and wherein the input to the computing platform is further based on the position signal provided by the accelerometer and/or the gyroscope.

10. The pressure sensitive peripheral device of claim 1, wherein the electronic circuitry is further configured to receive multiple contemporaneous pressure signals provided by the one or more pressure sensors and to interpret the multiple contemporaneous pressure signals for providing the input to the computing platform.

11. The pressure sensitive peripheral device of claim 1, wherein the electronic circuitry is further configured to quantify the compressive pressure applied to the housing body.

12. The pressure sensitive peripheral device of claim 1, further comprising:
   a heart rate sensor disposed within the housing body, the heart rate sensor being configured to provide a heart rate signal of a user of the pressure sensitive peripheral device;
   a blood pressure sensor disposed with the housing body, the blood pressure sensor being configured to provide a signal measuring a blood pressure of the user of the pressure sensitive peripheral device; and/or a vibration sensor disposed within the housing body, the vibration sensor being configured to provide a vibrating signal conveying information indicating a vibration of the pressure sensitive peripheral device; and, wherein the electronic circuitry is further configured to process the heart rate signal, the signal measuring the blood pressure of the user, and/or the vibration signal for generating the control input.

13. The pressure sensitive peripheral device of claim wherein the pressure sensitive peripheral device includes a computer mouse, a trackball, a joystick, a gamepad, a driving wheel, or a remote control.

14. The pressure sensitive peripheral device of claim 1, wherein the electronic circuitry is disposed within the pressure sensitive peripheral device.

15. The pressure sensitive peripheral device of claim 1, wherein the electronic circuitry is disposed within the computing platform.

16. A system for facilitating receipt of user inputs through a pressure sensitive peripheral device, the pressure sensitive peripheral device having a housing body with one or more pressure sensors disposed therein, the system comprising
one or more physical processors configured to execute computer program instructions to cause the one or more physical processors to:
receive, from the one or more pressure sensors, a pressure signal which is constant or variable in time conveying information associated with a compressive pressure applied to the housing body of the pressure sensitive peripheral device, the pressure signal being provided responsive to a first set of two opposing forces applied to the housing body, wherein the first set of two opposing forces does not perform a clicking motion; and
responsive to receiving the pressure signal provided by the one or more pressure sensors, provide an input to a computing platform based on the received pressure signal, the input being provided to facilitate controlling a graphical user interface presented on a display associated with the computing platform in accordance with a fitness exercise shown by the graphical user interface,
wherein providing the input to the computing platform based on the received pressure signal provided by the one or more pressure sensors comprises determining whether the compressive pressure applied to the housing body has reached a minimum magnitude that corresponds to a minimum physical exercise level, and only providing the input to the computing platform responsive to the compressive pressure reaching the minimum magnitude, wherein the fitness exercise is an isometric exercise performed through the pressure sensitive peripheral device by squeezing and/or moving the pressure sensitive peripheral device such that an indicator shown by the graphical user interface moves along a curve line displayed by the graphical user interface for a time period.

17. The system of claim 16, wherein the one or more processors are further configured to execute computer program instructions to cause the one or more physical processors to provide a second pressure signal conveying information associated with a second compressive pressure applied to the housing body, the second pressure signal being provided responsive to a second set of two opposing forces applied to parts of the housing body, wherein the second set of two opposing forces are separate and discrete from the first set of two opposing forces.

18. The system of claim 16, wherein providing the input to the computing platform based on the received pressure signal provided by the one or more pressure sensors comprises determining whether the compressive pressure applied to the housing body has breached a threshold minimum magnitude level that corresponds to the minimum physical exercise level.

19. The system of claim 16, wherein controlling the graphical user interface presented on the display associated with the computing platform as facilitated by the provided input also includes one or more of:
input of a value in the graphical user interface;
selection from a menu in the graphical user interface;
scrolling the graphical user interface;
moving a pointer in the graphical user interface;
manipulation of a virtual object in the graphical user interface;
entry of a password or a code in the graphical user interface;
interaction with a rehabilitation program through the graphical user interface;
interaction with a medical treatment program through the graphical user interface; and
interaction with a game through the graphical user interface.

20. The system of claim 19, wherein interaction with the game includes performing one or more game actions through the pressure sensitive peripheral device.

21. The system of claim 16, wherein the one or more processors are further configured to execute computer program instructions to cause the one or more physical processors to receive multiple contemporaneous pressure signals provided by the one or more pressure sensors and to interpret the multiple contemporaneous pressure signals for providing the input to the computing platform.

22. A method for facilitating receipt of user inputs through a pressure sensitive peripheral device, the pressure sensitive peripheral device having a housing body with one or more pressure sensors disposed therein, the method being implemented in one or more physical processors configured to execute computer instructions, the method comprising:
providing, with the one or more pressure sensors, a pressure signal which is constant or variable in time conveying information associated with a compressive pressure applied to the housing body of the pressure sensitive peripheral device, the pressure signal being provided responsive to the housing body being squeezed by a first set of two opposing forces applied to the housing body, wherein the first set of two opposing forces does not perform a clicking motion;
receiving, with the one or more physical processors, the pressure signal provided by the one or more pressure sensors in contact with the housing; and
responsive to receiving the pressure signal provided by the one or more pressure sensors, providing, with the one or more physical processors, a control input to a computing platform based on the received pressure signal, the input being provided to facilitate controlling a graphical user interface presented on a display associated with the computing platform in accordance with a fitness exercise shown by the graphical user interface,
wherein providing the input to the computing platform based on the received pressure signal provided by the one or more pressure sensors comprises determining whether the compressive pressure applied to the housing body has reached a minimum magnitude that corresponds to a minimum physical exercise level, and only providing the input to the computing platform responsive to the compressive pressure reaching the minimum magnitude, wherein interaction with the fitness exercise is an isometric exercise performed through the pressure sensitive peripheral device by squeezing and/or moving the pressure sensitive peripheral device such that an indicator displayed by the graphical user interface moves along a curve line displayed by the graphical user interface for a time period.

23. The method of claim 22, further comprising providing a second pressure signal conveying information associated with a second compressive pressure applied to the housing body, the second pressure signal being provided responsive to a second set of two opposing forces applied to parts of the housing body, wherein the second set of two opposing forces are separate and discrete from the first set of two opposing forces.

24. The method of claim 22, wherein providing the input to the computing platform based on the received pressure signal provided by the one or more pressure sensors comprises determining whether the compressive pressure applied to the housing body has breached a threshold minimum magnitude level that corresponds to the minimum physical exercise level.

25. The method of claim 22, wherein controlling the graphical user interface presented on the display associated with the computing platform as facilitated by the provided input also includes one or more of:
  input of a value in the graphical user interface;
  selection from a menu in the graphical user interface;
  scrolling the graphical user interface;
  moving a pointer in the graphical user interface;
  manipulation of a virtual object in the graphical user interface;
  entry of a password or a code in the graphical user interface;
  interaction with a rehabilitation program through the graphical user interface;
  interaction with a medical treatment program through the graphical user interface; and
  interaction with a game through the graphical user interface.

26. The method of claim 25, wherein interaction with the game includes performing one or more game actions through the pressure sensitive peripheral device.

27. The method of claim 22, further comprising receiving multiple contemporaneous pressure signals provided by the one or more pressure sensors and to interpret the multiple contemporaneous pressure signals for providing the input to the computing platform.

* * * * *